(12) United States Patent
Fung et al.

(10) Patent No.: US 6,518,475 B2
(45) Date of Patent: Feb. 11, 2003

(54) PROCESS FOR MAKING ETHYLENE AND PROPYLENE

(75) Inventors: Shun C. Fung, Bridgewater, NJ (US); Chunshe Cao, Kennewick, WA (US); Teng Xu, Houston, TX (US)

(73) Assignee: ExxonMobil Chemical Patents Inc., Houston, TX (US)

(*) Notice: Subject to any disclaimer, the term of this patent is extended or adjusted under 35 U.S.C. 154(b) by 0 days.

(21) Appl. No.: 09/785,409

(22) Filed: Feb. 16, 2001

(65) Prior Publication Data

US 2002/0143221 A1 Oct. 3, 2002

(51) Int. Cl.$^7$ ................................................ C07C 1/00
(52) U.S. Cl. ........................ 585/640; 585/638; 585/639; 585/904
(58) Field of Search .................... 585/638, 634, 585/640, 904

(56) References Cited

U.S. PATENT DOCUMENTS

| | | | |
|---|---|---|---|
| 2,768,127 A | 10/1956 | Kimberlin, Jr. et al. | 196/55 |
| 3,258,455 A | 6/1966 | Natta et al. | 260/93.7 |
| 3,305,538 A | 2/1967 | Natta et al. | 260/93.7 |
| 3,364,190 A | 1/1968 | Emrick | 260/93.7 |
| 3,645,992 A | 2/1972 | Elston | 260/80.78 |
| 3,785,782 A | 1/1974 | Cartmell | 23/288 |
| 4,035,284 A | 7/1977 | Gross et al. | 208/120 |
| 4,076,698 A | 2/1978 | Anderson et al. | 526/348.6 |
| 4,076,796 A | 2/1978 | Reh et al. | 423/659 |
| 4,134,926 A | 1/1979 | Tsao et al. | 260/682 |
| 4,229,608 A | 10/1980 | Chen et al. | 585/640 |
| 4,243,691 A | 1/1981 | Mohlenkamp, Jr. et al. | 426/649 |
| 4,302,565 A | 11/1981 | Goeke et al. | 526/88 |
| 4,404,095 A | 9/1983 | Haddad et al. | 208/161 |
| 4,419,221 A | 12/1983 | Castagnos, Jr. et al. | 208/113 |
| 4,440,871 A | 4/1984 | Lok et al. | 502/214 |
| 4,499,327 A | 2/1985 | Kaiser | 585/640 |
| 4,552,645 A | 11/1985 | Gartside et al. | 208/80 |
| 4,659,685 A | 4/1987 | Coleman, III et al. | 502/113 |
| 4,664,888 A | 5/1987 | Castagnos, Jr. | 422/147 |
| 4,677,242 A | 6/1987 | Kaiser | 585/638 |
| 4,677,243 A | 6/1987 | Kaiser | 585/638 |
| 4,752,651 A | 6/1988 | Kaiser | 585/638 |
| 4,780,196 A | 10/1988 | Alagy et al. | 208/130 |
| 4,814,067 A | 3/1989 | Gartside et al. | 208/127 |
| 4,861,743 A | 8/1989 | Flank et al. | 502/214 |
| 4,861,938 A | 8/1989 | Lewis et al. | 585/640 |
| 4,973,792 A | 11/1990 | Lewis et al. | 585/638 |
| 5,095,163 A | 3/1992 | Barger | 585/640 |
| 5,096,684 A | 3/1992 | Guth et al. | 423/306 |
| 5,126,308 A | 6/1992 | Barger et al. | 502/214 |
| 5,191,141 A | 3/1993 | Barger et al. | 585/640 |
| 5,343,830 A | 9/1994 | Alexander et al. | 122/4 |
| 5,714,662 A | 2/1998 | Vora et al. | 585/640 |
| 5,714,663 A | 2/1998 | Serrand et al. | 585/648 |
| 5,892,079 A | 4/1999 | Wilson, Jr. | 556/11 |
| 5,925,800 A | 7/1999 | Sun et al. | 585/640 |
| 5,952,538 A | 9/1999 | Vaughn et al. | 585/640 |
| 5,972,203 A | 10/1999 | Smith et al. | 208/113 |
| 6,023,005 A | 2/2000 | Lattner et al. | 585/639 |
| 6,121,503 A | 9/2000 | Janssen et al. | 585/640 |
| 6,121,504 A | 9/2000 | Kuechler et al. | 585/640 |
| 6,137,022 A | 10/2000 | Kuechler et al. | 585/638 |
| 6,166,282 A | 12/2000 | Miller | 585/638 |
| 6,174,339 B1 | 1/2001 | Varady | 55/348 |

FOREIGN PATENT DOCUMENTS

| | | |
|---|---|---|
| EP | 0 359 841 B1 | 8/1993 |
| JP | 096 996 | 12/1983 |

OTHER PUBLICATIONS

Blackwell et al., *Solid–State MNR of Silicoaluminophosphate Molecular Sieves and Aluminophosphate Materials*, J. Phys. Chem., vol. 92, pp. 3965–3970 (1988).
Zenz et al., *Riser Reactor*, Fluidization and Fluid–Particle Systems, Reinhold Publishing Corp. NY, pp. 48–59 (1960).
Kunii et al., *Free Fall Reactor*, Fluidization Engineering, Robert E. Krieger Publishing Co. NY, (1977).
Meier et al., *Atlas of Zeolite Structural Types*, Butterworth Heineman, 4th ed., (1996).
"MTO—has its time come?" Nitrogen & Methanol, No. 246, (Jul.–Aug. 2000).
Barger et al., "Converting Natural Gas to Ethylene and Propylene by the UOP/Hydro MTO Process," 12$^{th}$ International Zeolite Conference Materials Research Society p. 567–573 (1999).
Chang, "Methanol Conversion to Light Olefins," Catal. Rev.–Sci. Eng., 26(3&4), 323–345 (1984).
Kaeding et al., "Production of Chemicals from Methanol," Journal of Catalysis 61, 155–164 (1980).

*Primary Examiner*—Thuan D. Dang
(74) *Attorney, Agent, or Firm*—Paul T. LaVoie (57) ABSTRACT

A process for increasing the ethylene selectivity of a silicoaluminophosphate molecular sieve catalyst by using acetone in an oxygenate conversion process. Acetone can be added with the oxygenate feed at a concentration from about 1% to about 15% by weight, preferably about 1% to about 8% by weight, more preferably about 2% to about 5% by weight. Alternatively, acetone can be added as a pre-feed to the molecular sieve catalyst, particularly regenerated and fresh catalyst, in an contact zone. The pre-feed contacted catalyst is then directed to an oxygenate conversion zone. The acetone concentration in the pre-feed is from about 1% to about 99% by weight, preferably about 30% to about 70% by weight.

15 Claims, 2 Drawing Sheets

PROCESS FOR MAKING ETHYLENE AND PROPYLENE

FIELD OF THE INVENTION

The present invention is directed to a method of converting an oxygenate feed to an olefin product using a silicoaluminophosphate molecular sieve catalyst.

BACKGROUND OF THE INVENTION

Ethylene is an important petrochemical. In 1998 about 80 million tons of ethylene were produced, and demand is expected to reach 100 million tons by 2003. The primary use for ethylene is as a monomer for the production of low and high density polyethylene. Approximately 60% of world ethylene consumption goes into making polyethylene for such products as plastic films, containers, and coatings. Other uses include the production of vinyl chloride, ethylene oxide, ethylbenzene and alcohols. Presently, about 90% of the ethylene is produced by the steam cracking of light paraffin, naptha, and gas oil.

Propylene is another important raw material. In 1998 about 46 million tons of propylene were produced, and demand is expected to reach 60 million tons by 2003. About 55% of the world consumption is directed to the production of polypropylene. Other important end products include acrylonitrile for acrylic and nylon fibers, and propylene oxide for polyurethane foams. About two-thirds of the propylene is produced from steam cracking petroleum feedstock, and the remaining third as a by-product of FCC gasoline refining.

A potential alternative to producing ethylene and propylene from petroleum feedstock is to use an oxygenate feedstock. A particularly promising oxygenate feedstock is methanol. Methanol is readily produced from synthesis gas, which is derived from the reforming of natural gas. Large scale production of methanol from "stranded" natural gas may provide methanol at a price that would allow methanol to be economically competitive with petroleum feedstock for the production of ethylene and propylene.

One way of producing ethylene and propylene is by the catalytic conversion of methanol using a silicoaluminophosphate (SAPO) molecular sieve catalyst. For example, U.S. Pat. No. 4,499,327 to Kaiser, discloses making olefins from methanol using any of a variety of SAPO molecular sieve catalysts. The advantage of using SAPO based catalysts, particularly SAPO-34 based catalysts, is that such catalysts have relatively high ethylene and propylene selectivities. However, SAPO catalysts undergo relatively rapid deactivation due to coke formation.

If an oxygenate, such as methanol, is to be used as a source of ethylene and propylene, improved catalysts or process conditions are needed to increase the production of ethylene from a given amount of oxygenate. This invention describes a process to increase ethylene selectivity in an oxygenate to olefin conversion process.

SUMMARY OF THE INVENTION

The invention is directed to a process of increasing the ethylene selectivity of an olefin product in an oxygenate to olefin conversion process by using an oxygenate feed containing methanol and acetone. The method includes contacting a silicoaluminophosphate molecular sieve catalyst with an oxygenate, preferably methanol, to convert a portion of the oxygenate to a product containing olefin, the oxygenate feed comprising from about 1% to about 15% by weight, preferably from about 1% to about 8% by weight, more preferably from about 2% to about 5% by weight acetone, and separating the ethylene and propylene from the olefin product. The method may further include recovering a portion of unreacted acetone. Preferably, the unreacted acetone is recovered as a dilute acetone stream, which is then directed to the oxygenate feed or oxygenate conversion zone.

The invention is also directed to a process of increasing ethylene selectivity in the olefin product by contacting silicoaluminophosphate molecular sieve catalyst, particularly regenerated and fresh catalyst, with a pre-feed containing acetone in a contact zone. The pre-feed contacted catalyst is then directed to an oxygenate conversion zone. The method includes contacting regenerated, SAPO molecular sieve catalyst, and optionally fresh catalyst, with a pre-feed containing acetone in a contact zone, directing the acetone contacted catalyst and an oxygenate to an oxygenate conversion zone to produce an olefin product, and separating the ethylene and propylene from the olefin product. The method may further include recovering a portion of unreacted acetone. Preferably, the unreacted acetone is recovered as a dilute acetone stream, which is then directed to the contact zone or oxygenate conversion zone. Also, the method may include separating a portion of the hydrocarbon product exiting the contact zone from the acetone contacted catalyst.

The pre-feed may further comprise methanol, ethanol, propanol, ethylene, propylene, butenes, or a mixture thereof. The pre-feed contains from about 1% to about 99% by weight, more preferably from about 30% to about 70% by weight, acetone. The amount of pre-feed added to the regenerated catalyst, and optionally fresh catalyst, is from about 2% to about 60% by weight, preferably from about 2% to about 20% by weight, most preferably from about 4% to about 12% by weight, $CH_2$ per weight of catalyst.

The present invention will be better understood by reference to the Detailed Description of the Invention when taken together with the attached drawings and appended claims

DETAILED DESCRIPTION OF THE INVENTION

The invention is directed to a process which increases the productivity to olefin and the selectivity to ethylene of a silicoaluminophosphate molecular sieve catalyst in an oxygenate to olefin conversion process. The increase in ethylene selectivity is associated with a decrease in butenes selectivity and little or no decrease in propylene selectivity. The process includes adding acetone with an oxygenate, preferably methanol. The concentration of the acetone in the oxygenate feed is from about 1% to about 15% by weight, preferably from about 1% to about 8% by weight, more preferably from about 2% to about 5% by weight. Although higher concentrations of acetone in the oxygenate feed can be used, the upper limit is restricted by engineering and cost efficiencies. As the acetone concentration exceeds about 15%, the total oxygenate conversion in the process decreases. Relative to methanol, acetone has a low conversion rate to product. For example, while methanol conversion rates of 90% to 100% are typical for an oxygenate to olefin process, acetone exhibits a conversion rate of about 5% to 20%. As a result, the amount of acetone that would have to be recovered and recycled in the process would overburden the process from the standpoint of equipment and operation costs.

In another embodiment, a pre-feed containing acetone can be used to increase ethylene selectivity. The term pre-feed is defined as a feed that contains acetone which contacts catalyst from the regenerator and/or fresh catalyst before the catalyst is directed to an oxygenate conversion zone. Other oxygenates, such as methanol, and/or diluents, such as water, can be added along with the acetone in the pre-feed. All or a portion of catalyst from the regenerator is contacted with a pre-feed containing acetone in a contact zone before directing the regenerated catalyst to an oxygenate conversion zone. Fresh catalyst may also be directed to the contact zone prior to contacting the oxygenate, preferably methanol. The pre-feed may optionally contain one or more hydrocarbons selected from the lower alcohols, ethers, or mixtures thereof. The lower alcohols may include methanol, ethanol, and/or propanol. The pre-feed may also include significant quantities of a diluent, e.g., water.

In one embodiment the pre-feed contains 100% by weight acetone. In another embodiment the pre-feed contains acetone and a lower alcohol, e.g., methanol. If a mixture of acetone and a lower alcohol is used, the mixture will contain from about 1% to about 99% by weight acetone, preferably from about 30% to about 70% by weight acetone. Because the pre-feed may also contain significant quantities of water, the stated weight percents are exclusive of the water present.

The acetone content in the pre-feed can be high as 100% acetone because the amount by weight of pre-feed is substantially less than the amount of oxygenate used in the process. As a result, the amount of acetone in the total oxygenate feed in the process is maintained below about 15% by weight.

One molecular sieve catalyst that may be used in this invention is one that incorporates a silicoaluminophosphate (SAPO) molecular sieve. The molecular sieve comprises a three-dimensional microporous crystal framework structure of $[SiO_2]$, $[AlO_2]$ and $[PO_2]$ corner sharing tetrahedral units. The way Si is incorporated into the structure can be determined by $^{29}Si$ MAS NMR. See Blackwell and Patton, *J. Phys. Chem.*, 92, 3965 (1988). The desired SAPO molecular sieves will exhibit one or more peaks in the $^{29}Si$ MAS NMR, with a chemical shift $\delta(Si)$ in the range of −88 to −96 ppm and with a combined peak area in that range of at least 20% of the total peak area of all peaks with a chemical shift $\delta(Si)$ in the range of −88 ppm to −115 ppm, where the $\delta(Si)$ chemical shifts refer to external tetramethylsilane (TMS).

It is preferred that the silicoaluminophosphate molecular sieve used in this invention have a relatively low $Si/Al_2$ ratio. In general, the lower the $Si/Al_2$ ratio, the lower the $C_1$–$C_4$ saturates selectivity, particularly propane selectivity. A $Si/Al_2$ ratio of less than 0.65 is desirable, with a $Si/Al_2$ ratio of not greater than 0.40 being preferred, and a $Si/Al_2$ ratio of not greater than 0.32 being particularly preferred.

Silicoaluminophosphate molecular sieves are generally classified as being microporous materials having 8, 10, or 12 membered ring structures. These ring structures can have an average pore size ranging from about 3.5 Å to about 15 Å. Preferred are the small pore SAPO molecular sieves having an average pore size of less than about 5 Å, preferably an average pore size ranging from about 3.5 Å to about 5 Å, more preferably from about 3.5 Å to about 4.2 Å. These pore sizes are typical of molecular sieves having 8 membered rings.

In general, silicoaluminophosphate molecular sieves comprise a molecular framework of corner-sharing $[SiO_2]$, $[AlO_2]$, and $[PO_2]$ tetrahedral units. This type of framework is effective in converting various oxygenates into olefin products.

The $[PO_2]$ tetrahedral units within the framework structure of the molecular sieve of this invention can be provided by a variety of compositions. Examples of these phosphorus-containing compositions include phosphoric acid, organic phosphates such as triethyl phosphate, and aluminophosphates. The phosphorous-containing compositions are mixed with reactive silicon and aluminum-containing compositions under the appropriate conditions to form the molecular sieve.

The $[AlO_2]$ tetrahedral units within the framework structure can be provided by a variety of compositions. Examples of these aluminum-containing compositions include aluminum alkoxides such as aluminum isopropoxide, aluminum phosphates, aluminum hydroxide, sodium aluminate, and pseudoboehmite. The aluminum-containing compositions are mixed with reactive silicon and phosphorus-containing compositions under the appropriate conditions to form the molecular sieve.

The $[SiO_2]$ tetrahedral units within the framework structure can be provided by a variety of compositions. Examples of these silicon-containing compositions include silica sols and silicium alkoxides such as tetra ethyl orthosilicate. The silicon-containing compositions are mixed with reactive aluminum and phosphorus-containing compositions under the appropriate conditions to form the molecular sieve.

Substituted SAPOs can also be used in this invention. These compounds are generally known as MeAPSOs or metal-containing silicoaluminophosphates. The metal can be alkali metal ions (Group IA), alkaline earth metal ions (Group IIA), rare earth ions (Group IIIB, including the lanthanide elements: lanthanum, cerium, praseodymium, neodymium, samarium, europium, gadolinium, terbium, dysprosium, holmium, erbium, thulium, ytterbium and lutetium; and scandium or yttrium) and the additional transition cations of Groups IVB, VB, VIB, VIIB, VIIIB, and IB.

Preferably, the Me represents atoms such as Zn, Mg, Mn, Co, Ni, Ga, Fe, Ti, Zr, Ge, Sn, and Cr. These atoms can be inserted into the tetrahedral framework through a $[MeO_2]$ tetrahedral unit. The $[MeO_2]$ tetrahedral unit carries a net electric charge depending on the valence state of the metal substituent. When the metal component has a valence state of +2, +3, +4, +5, or +6, the net electric charge is between −2 and +2. Incorporation of the metal component is typically accomplished adding the metal component during synthesis of the molecular sieve. However, post-synthesis ion exchange can also be used. In post synthesis exchange, the metal component will introduce cations into ion-exchange positions of the molecular sieve.

Suitable silicoaluminophosphate molecular sieves include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof. Preferred are SAPO-17, SAPO-18, SAPO-34, SAPO-35, SAPO-44 SAPO-47, and SAPO-56, particularly SAPO-18 and SAPO-34, including the metal containing forms thereof, and mixtures thereof. As used herein, the term mixture is synonymous with combination and is considered a composition of matter having two or more components in varying proportions, regardless of their physical state.

The silicoaluminophosphate molecular sieves are synthesized by hydrothermal crystallization methods generally known in the art. See, for example, U.S. Pat. Nos. 4,440,871; 4,861,743; 5,096,684; and 5,126,308. A reaction mixture is formed by mixing together reactive silicon, aluminum and phosphorus components, along with at least one template. Generally the mixture is sealed and heated, preferably under autogenous pressure, to a temperature of at least 100° C., preferably from about 100° C. to about 250° C., until a crystalline product is formed. Formation of the crystalline product can take anywhere from around 2 hours to as much as 2 weeks. In some cases, stirring or seeding with crystalline material will facilitate the formation of the product.

Typically, the molecular sieve product is formed in solution. It can be recovered by standard means, such as by centrifugation or filtration. The product can also be washed, recovered by the same means, and dried.

As a result of the crystallization process, the recovered sieve contains within its pores at least a portion of the template used in making the initial reaction mixture. The crystalline structure essentially wraps around the template, and the template must be removed so that the molecular sieve can exhibit catalytic activity. Once the template is removed, the crystalline structure that remains has what is typically called an intracrystalline pore system.

In many cases, depending upon the nature of the final product formed, the template may be too large to be eluted from the intracrystalline pore system. In such a case, the template can be removed by a heat treatment process. For example, the template can be calcined, or essentially combusted, in the presence of an oxygen-containing gas, by contacting the template-containing sieve in the presence of the oxygen-containing gas and heating at temperatures from about 200° C. to about 900° C. In some cases, it may be desirable to heat in an environment having a low oxygen concentration. In these cases, however, the result will typically be a breakdown of the template into a smaller component, rather than by the combustion process. This type of process can be used for partial or complete removal of the template from the intracrystalline pore system. In other cases, with smaller templates, complete or partial removal from the sieve can be accomplished by conventional desorption processes such as those used in making standard zeolites.

The reaction mixture can contain one or more templates. Templates are structure directing or affecting agents, and typically contain nitrogen, phosphorus, oxygen, carbon, hydrogen or a combination thereof, and can also contain at least one alkyl or aryl group, with 1 to 8 carbons being present in the alkyl or aryl group. Mixtures of two or more templates can produce mixtures of different sieves or predominantly one sieve where one template is more strongly directing than another.

Representative templates include tetraethyl ammonium salts, cyclopentylamine, aminomethyl cyclohexane, piperidine, triethylamine, cyclohexylamine, tri-ethyl hydroxyethylamine, morpholine, dipropylamine (DPA), pyridine, isopropylamine and combinations thereof. Preferred templates are triethylamine, cyclohexylamine, piperidine, pyridine, isopropylamine, tetraethyl ammonium salts, dipropylamine, and mixtures thereof. The tetraethylammonium salts include tetraethyl ammonium hydroxide (TEAOH), tetraethyl ammonium phosphate, tetraethyl ammonium fluoride, tetraethyl ammonium bromide, tetraethyl ammonium chloride, tetraethyl ammonium acetate. Preferred tetraethyl ammonium salts are tetraethyl ammonium hydroxide and tetraethyl ammonium phosphate.

The SAPO molecular sieve structure can be effectively controlled using combinations of templates. For example, in a particularly preferred embodiment, the SAPO molecular sieve is manufactured using a template combination of TEAOH and dipropylamine. This combination results in a particularly desirable SAPO structure for the conversion of oxygenates, particularly methanol and dimethyl ether, to light olefins such as ethylene and propylene.

The molecular sieve catalysts are typically admixed (i.e., blended) with other materials. When blended, the resulting composition is typically referred to as a molecular sieve catalyst, with the catalyst comprising the zeolite or non-zeolitic molecular sieve.

Materials which can be blended with the molecular sieve can be various inert or catalytically active materials, or various binder materials. These materials include compositions such as kaolin and other clays, various forms of rare earth metals, metal oxides, other non-zeolite catalyst components, zeolite catalyst components, alumina or alumina sol, titania, zirconia, magnesia, thoria, beryllia, quartz, silica or silica or silica sol, and mixtures thereof. These components are also effective in reducing, inter alia, overall catalyst cost, acting as a thermal sink to assist in heat shielding the catalyst during regeneration, densifying the catalyst and increasing catalyst strength. It is particularly desirable that the inert materials that are used in the catalyst to act as a thermal sink have a heat capacity of from about 0.05 cal/g-° C. to about 1 cal/g-° C., more preferably from about 0.1 cal/g-° C. to about 0.8 cal/g-° C., most preferably from about 0.1 cal/g-° C. to about 0.5 cal/g-° C.

Additional molecular sieve materials can be included as a part of the molecular sieve catalyst composition or they can be used as separate molecular sieve catalysts in admixture with the molecular sieve catalyst if desired. Structural types of small pore molecular sieves that are suitable for use in this invention include AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof. Structural types of medium pore molecular sieves that are suitable for use in this invention include MFI, MEL, MTW, EUO, MTT, HEU, FER, AFO, AEL, TON, and substituted forms thereof. These small and medium pore molecular sieves are described in greater detail in the *Atlas of Zeolite Structural Types*, W. M. Meier and D. H. Olsen, Butterworth Heineman, 3rd ed., 1997. Preferred molecular sieves which can be combined with a silicoaluminophosphate catalyst include ZSM-5, ZSM-34, erionite, and chabazite.

The catalyst composition preferably comprises about from about 1% to about 99% by weight, more preferably from about 5% to about 90% by weight, and most preferably from about 10% to about 80% by weight, molecular sieve. In embodiments of the invention described in the working examples, the SAPO catalyst contained about 40% to about 60% by weight SAPO molecular sieve. The remainder of the catalyst contained an alumina binder and clay.

The catalyst can be subjected to a variety of treatments to achieve the desired physical and chemical characteristics. Such treatments include, but are not necessarily limited to hydrothermal treatment, calcination, acid treatment, base treatment, milling, ball milling, grinding, and combinations thereof.

Catalyst that has been previously exposed to an oxygenate feedstock will typically have a higher ethylene and/or propylene selectivity, and produce lower amounts of propane. However, as the catalyst is further exposed to the oxygenate, carbon deposits known as coke accumulate within the pores of the molecular sieve. This coke leads to a partial deactivation of the catalyst. As a result, the coke must be removed by contacting the catalyst with a regeneration medium.

In the process of this invention, a portion of feedstock exposed catalyst is regenerated by contacting the exposed catalyst with a regeneration medium to remove all or part of the coke deposits that accumulate within the pores of the molecular sieve. Regeneration of exposed catalyst will occur periodically or continuously outside the reactor by removing a portion of the exposed catalyst to a separate regenerator, and regenerating the coked catalyst in the regenerator. Regeneration can occur at times and conditions appropriate to maintain a desired level of coke on the catalyst within the reactor.

Following regeneration the catalyst can be directed back to the reactor for further conversion of oxygenate. However, regenerated catalyst is generally not as productive to olefin or as selective to ethylene as oxygenate exposed catalyst. The regeneration process removes most of the carbon from the pores of the oxygenate exposed catalyst, and an optimal catalyst for oxygenate conversion will have some portion of its pore structure filled with carbon. For this reason applicants sought ways to increase the productivity and selectivity of regenerated catalyst by reincorporating carbon in the pores of regenerated catalyst before the catalyst is directed to an oxygenate conversion zone. The introduction of acetone and regenerated catalyst into a contact zone according to the invention is one way of increasing olefin productivity and ethylene selectivity.

Like catalyst from the regenerator, fresh catalyst is not optimized for oxygenate conversion because it lacks sufficient carbon in the pore structure. Therefore, the invention is also directed to incorporating carbon in the pores of fresh catalyst before the catalyst is directed to an oxygenate conversion zone. Fresh catalyst is defined as catalyst that has yet to contact oxygenate in an oxygenate conversion reactor. Fresh catalyst is added to the oxygenate conversion process to make up for deactivated catalyst and catalyst fines that are removed from the process.

The invention provides an optimized process for the production of ethylene by contacting all or a portion of regenerated catalyst and/or fresh catalyst with a pre-feed containing acetone in a contact zone before directing the regenerated catalyst and/or fresh catalyst to the oxygenate conversion zone. A portion of the pre-feed is converted to the carbon disposed in the pores resulting in a more optimal catalyst for oxygenate conversion. Desirably, the carbon will be in the form of a single ring, aromatic hydrocarbon having one or more alkyl, preferably methyl, substituents.

Figure 1:
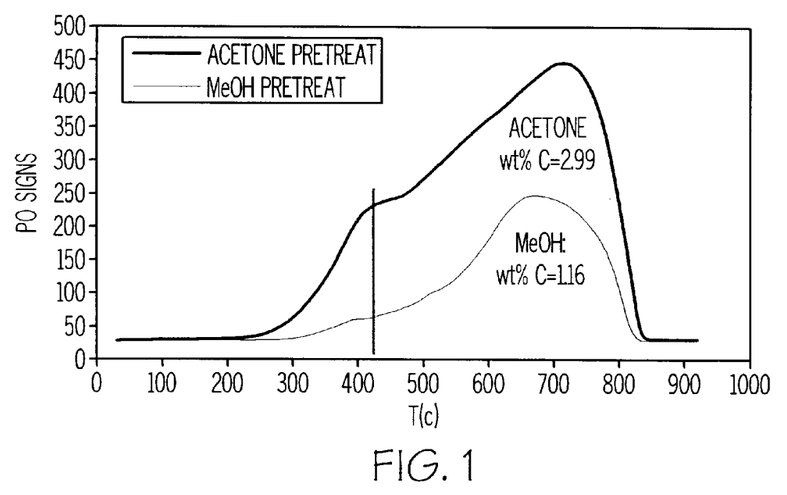
FIG. 1 is shows the Temperature Programmed Oxidation (TPO) profile of catalyst exposed to acetone and methanol in a contact zone.

FIG. 1 shows Temperature Programmed Oxidation (TPO) data of SAPO catalyst exposed to methanol. In one case the SAPO catalyst was previously exposed to acetone (acetone contains three $CH_2$ groups or 72% by weight $CH_2$, 8% by weight $CH_2$ per weight catalyst). In the other case the SAPO catalyst was previously exposed to methanol (methanol contains one $CH_2$ group or 44% by weight $CH_2$, 8% by weight $CH_2$ per weight catalyst). As shown, the SAPO catalyst exposed to acetone contains a higher carbon content on the catalyst than the methanol exposed catalyst. The higher initial carbon content on the acetone exposed catalyst results in a more selective catalyst to ethylene. The carbon content on the acetone exposed catalyst also tends to build at a greater rate than methanol exposed catalyst.

Figure 2:
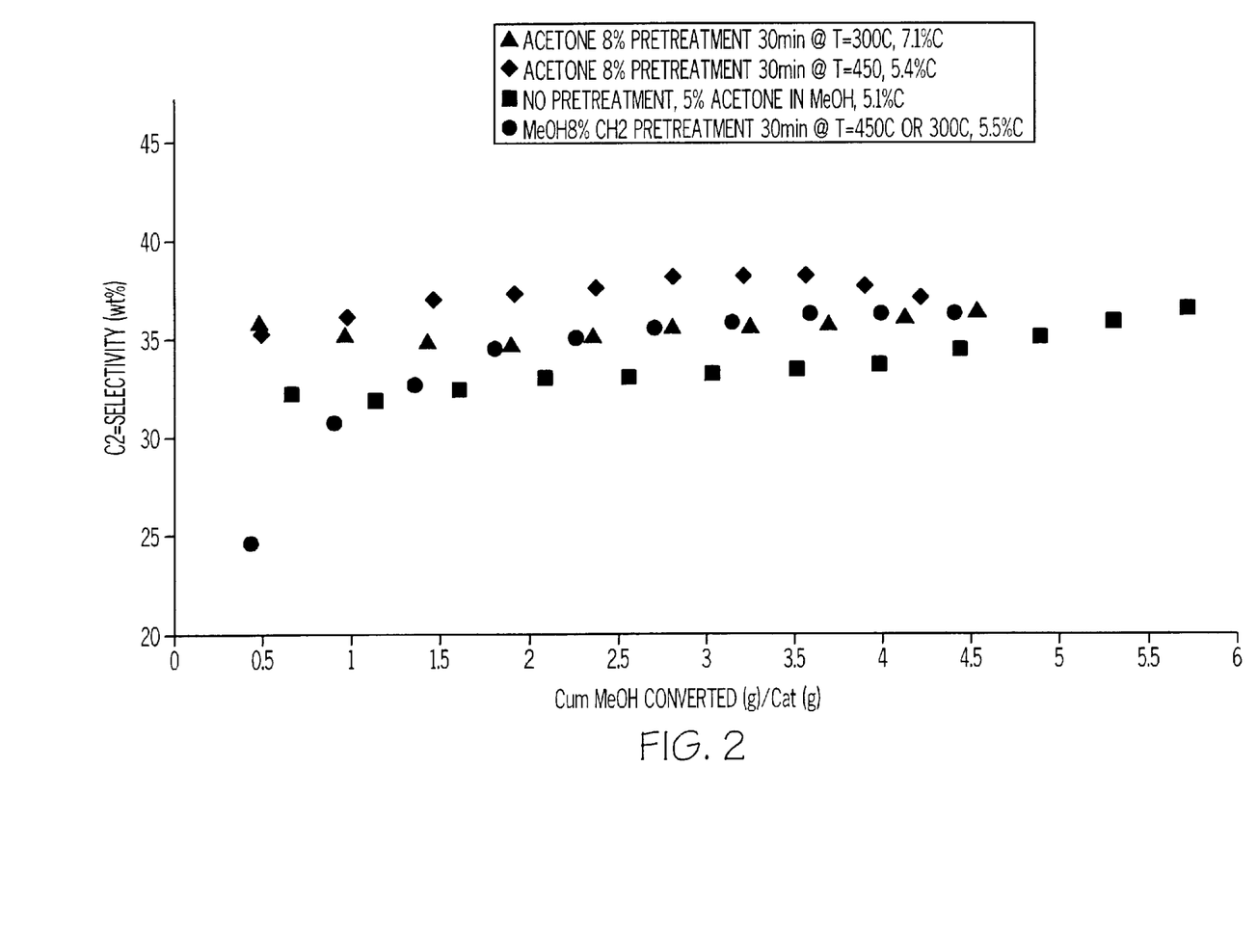
FIG. 2 is graph of ethylene selectivity data.

FIG. 2 shows the ethylene selectivity of fresh catalyst exposed to methanol in an oxygenate conversion zone under various catalyst contact conditions. FIG. 2 shows catalyst exposed to acetone at 300° C. and 450° C. in a contact zone, catalyst exposed to methanol at 450° C. in a contact zone, and catalyst exposed to an oxygenate feed containing 5% by weight acetone. The 300° C. and 450° C. acetone exposed catalyst exhibits about a 5% and about a 3% increase in ethylene selectivity, respectively, relative to the methanol exposed catalyst. The acetone exposed catalysts also exhibit a significant reduction in catalyst lifetime or a greater rate of coke buildup than the methanol exposed catalyst. The oxygenate feed containing 5% acetone exhibits about a 2% to 3% increase in ethylene selectivity, and only a slight reduction in catalyst lifetime relative to the methanol exposed catalyst. Therefore, FIG. 2 indicates that the ethylene selectivity of a SAPO catalyst can be increased by exposing SAPO catalyst to acetone. The exposure of the catalyst to acetone can take place in a contact zone with acetone in a pre-feed. Alternatively, exposure of the catalyst to acetone can take place in the oxygenate conversion zone with acetone in the oxygenate feed.

The amount of pre-feed, which includes acetone, and optionally other hydrocarbons, added to the contact zone can vary from about 2% to about 60% by weight $CH_2$ per weight of regenerated and fresh catalyst added to the contact zone. Preferably the amount of pre-feed added will vary from about 2% to about 20% by weight $CH_2$ per weight catalyst. More preferably the amount of pre-feed added will vary from about 4% to about 12% by weight $CH_2$ per weight catalyst. Acetone contains 72% by weight $CH_2$. Methanol contains 44% by weight $CH_2$. Ethanol contains two $CH_2$ groups or 61% by weight $CH_2$. Accordingly, the pre-feed will contain sufficient amounts of $CH_2$ to satisfy the catalyst feed to the contact zone for each of the stated ranges.

The pre-feed contains acetone and optionally one or more hydrocarbons selected from the lower alcohols, ethers, light olefins, ketones, and mixtures thereof. The lower alcohols may include methanol, ethanol, and/or propanol. In one embodiment the pre-feed contains about 100% by weight acetone. In another embodiment the pre-feed contains acetone and a lower alcohol, e.g., methanol. If a mixture of acetone and a lower alcohol is used, the mixture will contain from about 1% to about 99% by weight acetone, preferably from about 30% to about 70% by weight acetone.

It is to be understood that due to the hydroscopic nature of acetone and the lower alcohols, water may be contained within the pre-feed without significantly affecting the advantages of the invention. The amount of water in the pre-feed is exclusive to the stated weight percent ranges of the pre-feed.

In addition, because some of the acetone in the pre-feed is not converted to carbon deposits and acetone has a relatively low conversion rate to olefin, i.e., about 5% to 20%, the unconverted acetone can be recycled to the pre-feed. The more acetone that is recycled, the less fresh acetone is required to be added to the pre-feed. If recycled acetone is used as a portion of the pre-feed, the pre-feed will likely contain significant amounts of water because water is a major by-product of the oxygenate to olefin process. The recycled acetone may also contain large quantities of unreacted methanol and dimethyl ether. Acetone that is partially separated from the water and other conversion products is defined as a dilute acetone stream. A portion of this dilute acetone stream may be used to contact the regenerated catalyst in the contact zone.

Alternatively, the hydrocarbon product exiting the contact zone can be separated from the acetone contacted catalyst. The separated hydrocarbons can be further separated to remove the desired olefin products from the unreacted acetone. The unreacted acetone may then be recycled to the contact zone. The separated acetone contacted catalyst is directed to the oxygenate conversion zone.

In the preferred embodiment, an auxiliary reactor physically separated from the oxygenate conversion reactor is used as the contact zone. Desirably, the auxiliary reactor is a fluidized bed reactor operationally positioned between the oxygenate conversion reactor and the regenerator. The auxiliary reactor is capable of continuously receiving catalyst from the regenerator and subsequently supplying the acetone contacted catalyst to the oxygenate conversion reactor. The auxiliary reactor is also capable of continuously receiving fresh catalyst.

Generally, the temperature of the auxiliary reactor will be less than the temperature of the oxygenate conversion reactor. Preferably, the temperature of the auxiliary reactor is about 50° C. less than, more preferably about 80° C. less than, most preferably about 100° C. less than, the temperature of the oxygenate conversion reactor. In a preferred embodiment, the temperature in the auxiliary reactor is from about 150° C. to about 500° C., more preferably from about 200° C. to about 400° C., most preferably from about 250° C. to about 350° C.

Alternatively, a contact zone disposed adjacent to or within the oxygenate conversion reactor may substitute for the auxiliary reactor. The function of the contact zone is nearly identical to that of the auxiliary reactor. Generally, the temperature of the contact zone is less than the temperature in the oxygenate conversion zone of the reactor. Preferably, the temperature of the contact zone is about 50° C. less than, more preferably about 80° C. less than, most preferably about 100° C. less than, the temperature of the oxygenate conversion zone. In a preferred embodiment, the temperature in the contact zone is from about 150° C. to about 500° C., more preferably from about 200° C. to about 400° C., most preferably from about 250° C. to about 350° C.

The temperature of the contact zone may be controlled by introducing regenerated catalyst, pre-feed, and/or a dilute acetone stream into the contact zone of the oxygenate conversion reactor at one set of conditions. The pre-feed and/or the dilute acetone stream may optionally contain a diluent. Operating conditions in the oxygenate conversion zone may be maintained through control of the conditions at which the acetone contacted catalyst and oxygenate are introduced, including temperature, pressure or phase. Optionally, the contact and conversion zones may comprise separate heating or cooling functions such as steam or cooling water coils to control operation conditions in the two zones.

The pre-feed contacts regenerated catalyst, and optionally fresh catalyst, at a pressure from about 20 psia to about 1000 psia. Preferably, the pre-feed contacts the catalyst at a pressure from about 25 psia to about 500 psia, more preferably at a pressure from about 30 psia to about 200 psia.

The pre-feed contacts regenerated catalyst, and optionally fresh catalyst, at a weight hour space velocity (WHSV) from about 1 $hr^{-1}$ to about 500 $hr^{-1}$. Preferably, the pre-feed contacts the catalyst at WHSV from about 1 $hr^{-1}$ to about 100 $hr^{-1}$, more preferably at a WHSV from about 1 $hr^{-1}$ to about 50 $hr^{-1}$.

The oxygenate feedstock of this invention comprises at least one organic compound which contains at least one oxygen atom, e.g., the lower alcohols, ethers, ketone, and mixtures thereof. Examples of suitable oxygenate compounds include, but are not limited to: methanol; ethanol; n-propanol; dimethylether; and mixtures thereof. Preferred oxygenate compounds are methanol, dimethylether, or a mixture thereof. Also, because the conversion of acetone in the contact zone is relatively low (2% to 20% conversion) a portion of the acetone in the pre-feed is directed to the oxygenate conversion zone with the acetone contacted catalyst.

One or more inert diluents may be present in the oxygenate feedstock and/or in the pre-feed directed to the contact zone. As defined herein, diluents are compositions which are essentially non-reactive across a molecular sieve catalyst, and primarily function to make the oxygenates in the feedstock less concentrated. Typical diluents include, but are not necessarily limited to helium, argon, nitrogen, carbon monoxide, carbon dioxide, water, paraffins (especially the alkanes such as methane, ethane, and propane), aromatic compounds, and mixtures thereof. The preferred diluents are water and nitrogen. Water can be injected in either liquid or vapor form. For example, the process may be conducted in the presence of water such that the molar ratio water to methanol in the oxygenate feed is from about 0.01 to about 10.

In another embodiment, the acetone is added with the oxygenate, preferably methanol. The concentration of the acetone in the oxygenate feed is from about 1% to about 15% by weight, preferably from about 1% to about 8% by weight, more preferably from about 2% to about 5% by weight. Because the conversion of acetone to olefin product in the oxygenate conversion zone is relatively low (2% to 20% conversion) most of the acetone can be recycled to the oxygenate feed. The more acetone that is recycled, the less fresh acetone is required to be added to the oxygenate feed. The recycled acetone will most likely contain significant amounts of water because water is a major by-product of the oxygenate to olefin process. The acetone may be partially separated from the water resulting in a dilute acetone stream that is then directed to the oxygenate feed.

Any standard reactor system can be used, including fixed bed, fluid bed or moving bed systems. Preferred reactors are co-current riser reactors and short contact time, countercurrent free-fall reactors. Desirably, the reactor is one in which an oxygenate feedstock can be contacted with a molecular sieve catalyst at a weight hourly space velocity (WHSV) of at least about 1 $hr^{-1}$, preferably in the range of from about 1 $hr^{-1}$ to about 1000 $hr^{-1}$, more preferably in the range of from about 20 $hr^{-1}$, to about 1000 $hr^{-1}$, and most preferably in the range of from about 20 $hr^{-1}$ to about 500 $hr^{-1}$. WHSV is defined herein as the weight of oxygenate, and hydrocarbon which may optionally be in the feed, per hour per weight of the molecular sieve content of the catalyst. Because the catalyst or the feedstock may contain other materials which act as inerts or diluents, the WHSV is calculated on the weight basis of the oxygenate feed, and any hydrocarbon which may be present, and the molecular sieve contained in the catalyst.

Preferably, the oxygenate feed is contacted with the catalyst when the oxygenate is in a vapor phase. Alternately, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions.

The process can generally be carried out at a wide range of temperatures. An effective operating temperature range can be from about 200° C. to about 700° C., preferably from about 300° C. to about 600° C., more preferably from about 350° C. to about 550° C. At the lower end of the temperature range, the formation of the desired olefin products may become markedly slow. At the upper end of the temperature range, the process may not form an optimum amount of product.

The pressure also may vary over a wide range, including autogenous pressures. Effective pressures may be in, but are not necessarily limited to, oxygenate partial pressures at least 1 psia, preferably at least 5 psia. The process is particularly effective at higher oxygenate partial pressures, such as an oxygenate partial pressure of greater than 20 psia. Preferably, the oxygenate partial pressure is at least 25 psia, more preferably at least 30 psia. For practical design purposes it is desirable to operate at a methanol partial pressure of not greater than 500 psia, preferably not greater than 400 psia, most preferably not greater than 300 psia.

The conversion of oxygenates to produce light olefins may be carried out in a variety of catalytic reactors. Reactor types include conventional reactors such as fixed bed reactors, fluid bed reactors, and riser reactors. These and other types of conventional reactors are described in *Fluidization Engineering*, D. Kunii and O. Levenspiel, Robert E. Krieger Publishing Co. N.Y., 1977. Preferred reactors are riser reactors. Conventional riser reactor design is further described in "Riser Reactor," *Fluidization and Fluid-Particle Systems*, pages 48–59, F. A. Zenz and D. F. Othmo, Reinhold Publishing Corp., N.Y. 1960.

In a preferred embodiment of the continuous operation, only a portion of the catalyst is removed from the reactor and sent to the regenerator to remove the accumulated coke deposits that result during the catalytic reaction. In the regenerator, the catalyst is contacted with a regeneration medium containing oxygen or other oxidants. Examples of other oxidants include $O_3$, $SO_3$, $N_2O$, $NO$, $NO_2$, $N_2O_5$, and mixtures thereof. It is preferred to supply $O_2$ in the form of air. The air can be diluted with nitrogen, $CO_2$, or flue gas, and steam may be added. Desirably, the $O_2$ concentration in the regenerator is reduced to a controlled level to minimize overheating or the creation of hot spots in the spent or deactivated catalyst. The deactivated catalyst also may be regenerated reductively with $H_2$, CO, mixtures thereof, or other suitable reducing agents. A combination of oxidative regeneration and reductive regeneration can also be employed.

In essence, the coke deposits are removed from the catalyst during the regeneration process, forming a regenerated catalyst. The regenerated catalyst is then returned to the reactor for further contact with feed. Typical regeneration temperatures are in the range of about 250° C. to about 700° C., desirably in the range of about 350° C. to about 700° C. Preferably, regeneration is carried out at a temperature range of about 450° C. to about 700° C.

It is desirable to strip at least some of the volatile organic components which may be adsorbed onto the catalyst or located within its microporous structure prior to entering the regenerator. This can be accomplished by passing a stripping gas over the catalyst in a stripper or stripping chamber, which can be located within the reactor or in a separate vessel. The stripping gas can be any substantially inert medium that is commonly used. Examples of stripping gas are steam, nitrogen, helium, argon, methane, $CO_2$, CO, flue gas, and hydrogen.

It may be desirable to cool at least a portion of the regenerated catalyst to a lower temperature before it is directed to the conversion reactor or to the contact zone. A heat exchanger located externally to the regenerator may be used to remove some heat from the catalyst after it has been withdrawn from the regenerator. Another way is to contact the regenerated catalyst with a dilute acetone stream containing significant quantities of water to cool the catalyst. When the regenerated catalyst is cooled, it is desirable to cool it to a temperature which is from about 20° C. to about 200° C. lower than the temperature of the catalyst withdrawn from the regenerator. More desirably, it is cooled to a temperature from about 100° C. to about 200° C. lower than the temperature of the catalyst withdrawn from the regenerator. Introducing the cooled catalyst into the conversion reactor or the contact zone is one way to control the average temperature in the conversion reactor or contact zone.

In an embodiment with a contact zone, the oxygenate conversion reactor and contact zone are configured such that the oxygenate feed contacts the acetone contacted catalyst before it is introduced to the oxygenate conversion reactor. In an alternative embodiment, the reactor and contact zone are configured such that the oxygenate feed contacts the acetone contacted catalyst after it is introduced to the oxygenate conversion reactor. In yet another embodiment, the oxygenate feed can be split such that oxygenate feed contacts acetone contacted catalyst before the contacted catalyst is introduced to the oxygenate conversion reactor and after the contacted catalyst has been introduced to the oxygenate conversion reactor.

In the embodiment where the acetone is added with the oxygenate the oxygenate conversion reactor and regenerator are configured such that the oxygenate feed contacts the regenerated catalyst before the catalyst is introduced to the oxygenate conversion reactor. In an alternative embodiment, the reactor and regenerator are configured such that the oxygenate contacts the regenerated catalyst after the catalyst is introduced to the conversion reactor. In yet another embodiment, the oxygenate feed can be split such that feed contacts regenerated catalyst before the catalyst is introduced to the oxygenate conversion reactor and after the catalyst has been introduced to the oxygenate conversion reactor.

It is preferred that the catalyst within the reactor have an average level of coke effective for selectivity to ethylene and/or propylene. Preferably, the average coke level on the catalyst will be from about 2 wt. % to about 30 wt. %, more preferably from about 2 wt. % to about 20 wt. %. In order to maintain this average level of coke on catalyst, the entire volume of catalyst can be partially regenerated under conditions effective to maintain the desired coke content on catalyst. It is preferred, however, to recycle only a portion of the coked catalyst for feed contact without regenerating. This recycle can be performed either internal or external to the reactor. The portion of coked catalyst to be regenerated is preferably regenerated under conditions effective to obtain a regenerated catalyst having a coke content of less than 2 wt. %, preferably less than 1.5 wt. %, and most preferably less than 1.0 wt. %.

In order to make up for any catalyst loss during the regeneration or reaction process, fresh catalyst can be added. Preferably, the fresh catalyst is added to the regenerated catalyst after it is removed from the regenerator, and then both are added to the conversion reactor or to the contact zone. Fresh catalyst can also be added to the conversion reactor independently of the regenerated or acetone contacted catalyst.

One skilled in the art will also appreciate that the olefins produced by the oxygenate-to-olefin conversion reaction of the present invention can be polymerized to form polyolefins, particularly polyethylene and polypropylene. Processes for forming polyolefins from olefins are known in the art. Catalytic processes are preferred. Particularly preferred are metallocene, Ziegler/Natta and acid catalytic systems. See, for example, U.S. Pat. Nos. 3,258,455; 3,305, 538; 3,364,190; 5,892,079; 4,659,685; 4,076,698; 3,645, 992; 4,302,565; and 4,243,691. In general, these methods involve contacting the olefin product with a polyolefin-forming catalyst at a pressure and temperature effective to form the polyolefin product.

A preferred polyolefin-forming catalyst is a metallocene catalyst.

The preferred temperature range of from 50° C. to 240° C. and the reaction can be carried out at low, medium or high pressure, being anywhere within the range of about 1 bar to 200 bars. For processes carried out in solution, an inert diluent can be used, and the preferred operating pressure range is between 10 bars and 150 bars, with a preferred temperature range of 120° C. to 230° C. For gas phase processes, it is preferred that the temperature generally be from 60° C. to 160° C., and that the operating pressure be between 5 bars and 50 bars.

In addition to polyolefins, numerous other olefin derivatives may be formed from the olefins recovered therefrom. These include, but are not limited to, aldehydes, alcohols, acetic acid, linear alpha olefins, vinyl acetate, ethylene dicholoride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes. The methods of manufacturing these derivatives are well known in the art, and therefore, are not discussed herein.

This invention will be better understood with reference to the following examples, which are intended to illustrate specific embodiments within the overall scope of the invention as claimed.

EXAMPLE 1

An experiment using a SAPO-34 catalyst (50% SAPO-34/50% binder) was carried out in a fluidized-batch-recirculating (FBR) reactor at a gas-recirculating rate of about 10 circulations per second. The circulation rate was much higher than the reaction rate, and the reactor was considered as a non-gradient batch reactor. The catalyst particles were placed in a basket bound by two sintered-porous metal disks. An impeller rotating at 6000–7000 rpm circulated the gas in the reactor from the top of the basket through the annulus space to the bottom of the basket. The gas entered the bottom of the basket at a speed sufficient to fluidize the catalyst particles. Catalyst particles were in turbulent fluidization condition with very limited amount of gas bubbles in the suspension. Gas residence time was controlled by time-programmed valves that emptied the reactor gas to a large vacuum vessel. A gas chromatograph (GC) sampling valve was equipped in the gas depressure path to capture a gas sample for product composition analysis.

The reactor was at 300° C. and was charged with 0.3 grams of the catalyst and enough argon to achieve 60 psia reactor pressure. This was to ensure that the circulation of the argon gas by the fast rotation of the impeller can fluidize the catalyst particles before the injection of 0.043 cm$^3$ acetone so that there are good contacts of the oxygenate with the fluidized catalyst particles. This amount of acetone corresponds to 8 wt. % CH$_2$ per gram of catalyst. The reaction time was controlled by venting the reactor gas, via an automated valve, passing a GC sampling valve to a vacuum vessel at a preset time of 30 minutes. After the acetone contact, the reactor was purged with argon to remove products formed in the contact step. The reactor was refilled with argon to 60 psia.

The acetone activated catalyst was evaluated for methanol conversion at 450° C. by injection of 0.2 cm$^3$ methanol in the reactor. Under this reaction condition, the partial pressure of methanol was 40 psia. Methanol was allowed to contact the catalyst for 14.5 seconds. This is equivalent to a space velocity of 130 hr$^{-1}$. After the reaction products were removed from the reactor, a second methanol injection was introduced into the reactor and the methanol was allowed to contact the catalyst particles for 14.5 seconds before the product gas was analyzed. This was repeated until the methanol conversion level dropped to 80 wt. % or below. The catalyst lifetime can be expressed in a dimensionless catalyst on-stream time as gram of methanol converted per gram of catalyst (g MeOH conv./g cat.), i.e., at any instant in time, it is measured as cumulated gram of methanol converted per gram of catalyst. At g MeOH conv./g cat.= 0.49 methanol conversion is 93.23 wt. %. It drops to 87.13 wt. % at g MeOH conv./g cat.=2.38. Further increase in g MeOH conv./g cat. to 4.22 lowers the methanol conversion to 59.44 wt. %. The product selectivities are listed in Table 1.

EXAMPLE 2

An experiment identical to Example 1 was conducted using 0.07 cm$^3$ methanol instead of acetone in the contact step. The 0.07 cm$^3$ of methanol provides 8 wt. % of CH$_2$ per gram of catalyst same as that in the acetone contact. We have determined that methanol contact at 300° C. and 450° C. showed little difference in activity and selectivity. After the methanol contact, the catalyst was evaluated for methanol conversion at 450° C. under the same condition as in Example 1. At 4 g MeOH conv./g cat. the acetone activated catalyst exhibits a methanol conversion of about 60%. In comparison, the methanol activated catalyst exhibits a methanol conversion of about 92%, indicating a much better catalyst activity maintenance than the acetone activated catalyst. The product selectivities are listed in Table 1.

EXAMPLE 3

An experiment was carried out similar to Example 1. However, there is no catalyst contact step and 5 wt. % of acetone is added to the methanol feed. The reactor was first filled with argon to 60 psia and heated to 450° C. The impeller was in operation to fluidize the catalyst particles before the injection of 0.2 cm$^3$ of the methanol feed with the acetone additive into the reactor. The feed was allowed to contact the catalyst for 14.5 seconds. After the reaction products were removed from the reactor, a second feed injection was introduced into the reactor and the feed was allowed to contact the catalyst particles for 14.5 seconds before the product gas was analyzed. This was repeated until the methanol conversion level dropped to 80 wt. % or below. A comparison of the catalyst activity as a function of g MeOH conv./g cat. shows that the catalyst lifetime is greater with the acetone co-feed than the acetone activated catalyst. At a g MeOH conv./g cat. of 4.22 to 4.41, methanol conversion of the acetone additive is 80.68 wt. % as compared to 59.44 wt. % with the acetone activated catalyst.

The product selectivities of the acetone co-feed are listed in Table 1. On average, fresh catalyst that contacts acetone in an contact zone exhibits about 1% to 2.5% higher ethylene selectivity than fresh catalyst obtained from using an acetone co-feed. However, the acetone co-fed catalyst has a much greater catalyst lifetime.

Table 1 also compares the selectivity of fresh catalyst contacted with methanol in an contact zone with fresh catalyst that is contacted with an acetone co-feed and no prior acetone contact in an contact zone. It can be seen that at a on-stream time of 1.7, 2.8, and 4.0 g MeOH conv./g cat., the 5 wt. % acetone in methanol has a higher ethylene selectivity of 2.1%, 2.3%, and 2.6%, respectively than the catalyst that was contacted with methanol.

TABLE 1

| | gMeOH conv./g cat | | | | | | | | |
|---|---|---|---|---|---|---|---|---|---|
| | 1.7 | | | 2.8 | | | 4.0 | | |
| | Run mode | | | | | | | | |
| | AcO Act. | MeOH Act. | 5% AcO | AcO Act. | MeOH Act. | 5% AcO | AcO Act. | MeOH Act. | 5% AcO |
| Wt % MeOH Conversion | 91.1 | 92.0 | 92.8 | 83.5 | 91.2 | 90.1 | 59.4 | 90.0 | 83.5 |
| Methane selectivity, C1 | 0.58 | 0.54 | 0.54 | 0.79 | 0.52 | 0.58 | 1.3 | 0.57 | 0.72 |
| Ethylene selectivity, C2= | 36.9 | 32.4 | 34.5 | 38.1 | 33.2 | 35.5 | 37.1 | 33.7 | 36.3 |
| Ethane selectivity, C2 | 0.19 | 0.15 | 0.17 | 0.18 | 0.15 | 0.17 | 0.19 | 0.16 | 0.17 |

TABLE 1-continued

| | gMeOH conv./g cat | | | | | | | | |
|---|---|---|---|---|---|---|---|---|---|
| | 1.7 | | | 2.8 | | | 4.0 | | |
| | Run mode | | | | | | | | |
| | AcO Act. | MeOH Act. | 5% AcO | AcO Act. | MeOH Act. | 5% AcO | AcO Act. | MeOH Act. | 5% AcO |
| Propylene selectivity, C3 = | 44.5 | 44.8 | 44.7 | 44.4 | 45.4 | 44.9 | 45.2 | 45.4 | 45.1 |
| Propane selectivity, C3 | 0.25 | 0.39 | 0.32 | 0.20 | 0.28 | 0.23 | 0.03 | 0.23 | 0.18 |
| Butanes selectivity, C4 | 0.78 | 0.55 | 0.72 | 0.81 | 0.63 | 0.75 | 1.1 | 0.69 | 0.87 |
| Butenes selectivity, C4 = | 12.5 | 13.8 | 12.9 | 11.6 | 14.3 | 12.6 | 11.4 | 14.3 | 11.9 |
| C5 + selectivity | 4.3 | 7.4 | 6.1 | 3.9 | 5.5 | 5.3 | 3.7 | 4.9 | 4.8 |
| C2 = + C3 = selectivity | 81.4 | 77.2 | 79.2 | 82.5 | 78.6 | 80.4 | 82.3 | 79.2 | 81.4 |

AcO Act.: Catalyst activated by acetone; methanol feed at 450° C.
MeOH Act.: Catalyst activated by methanol; methanol feed at 450° C.
5% AcO: No Catalyst activation; methanol feed containing 5 wt % of acetone at 450° C.

Having now fully described this invention, it will be appreciated by those skilled in the art that the invention can be performed within a wide range of parameters within what is claimed, without departing from the spirit and scope of the invention.

What is claimed is:

1. A method of making ethylene and propylene comprising:
    contacting a silicoaluminophosphate molecular sieve catalyst with an oxygenate comprising at least one of methanol, ethanol, n-propanol, and dimethylether, to convert a portion of the oxygenate to an olefin product containing ethylene and propylene, the oxygenate further comprising about 1% to about 15% by weight acetone; and
    separating the ethylene and propylene from the olefin product.

2. The method of claim 1 wherein the oxygenate comprises about 1% to about 8% acetone.

3. The method of claim 2 wherein the oxygenate comprises about 2% to about 5% acetone.

4. The method of claim 1 wherein the silicoaluminophosphate molecular sieve catalyst is selected from the group consisting of SAPO-5, SAPO-17, SAPO-18, SAPO-20, SAPO-34, SAPO-44, SAPO-56, the metal containing forms of each thereof, and mixtures thereof.

5. The method of claim 1 wherein contacting the molecular sieve catalyst with the oxygenate comprises contacting the catalyst at a temperature from 350° C. to 550° C.

6. The method of claim 1 wherein the oxygenate comprises methanol.

7. The method of claim 1 wherein the oxygenate comprises a dilute acetone stream.

8. A method of making ethylene and propylene comprising:
    contacting regenerated, silicoaluminophosphate molecular sieve catalyst with a pre-feed comprising acetone in a contact zone;
    directing the acetone contacted catalyst and an oxygenate comprising at least one of methanol, ethanol, n-propanol, and dimethylether, to an oxygenate conversion zone to produce an olefin product; and
    separating the ethylene and propylene from the olefin product.

9. The method of claim 8 wherein the pre-feed further comprises methanol, ethanol, propanol, ethylene, propylene, butenes, or a mixture thereof.

10. The method of claim 8 wherein the pre-feed contains about 1% to about 99% acetone.

11. The method of claim 10 wherein the pre-feed contains about 30% to about 70% acetone.

12. The method of claim 8 further comprising recovering a portion of unreacted acetone in the olefin product and directing the recovered acetone to the contact zone.

13. The method of claim 8 wherein the silicoaluminophosphate molecular sieve catalyst is selected from the group consisting of SAPO-5, SAPO-17, SAPO-18, SAPO-20, SAPO-34, SAPO-44, SAPO-56, the metal containing forms of each thereof, and mixtures thereof.

14. The method of claim 8 further comprising separating a portion of hydrocarbons exiting the contact zone from the acetone contacted catalyst.

15. The method of claim 8 wherein the oxygenate comprises methanol.

* * * * *